(12) United States Patent
Ford

(10) Patent No.: US 11,590,107 B2
(45) Date of Patent: *Feb. 28, 2023

(54) METHODS FOR TREATING NEUROLOGICAL DISORDERS WITH $\alpha_{1A}$-AR PARTIAL AGONISTS

(71) Applicant: CURASEN THERAPEUTICS, INC., San Mateo, CA (US)

(72) Inventor: Anthony P. Ford, San Mateo, CA (US)

(73) Assignee: Curasen Therapeutics, Inc., San Mateo, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 17/079,263

(22) Filed: Oct. 23, 2020

(65) Prior Publication Data

US 2021/0121444 A1    Apr. 29, 2021

Related U.S. Application Data

(60) Provisional application No. 62/926,392, filed on Oct. 25, 2019.

(51) Int. Cl.
*A61K 31/4164* (2006.01)
*A61P 9/02* (2006.01)

(52) U.S. Cl.
CPC ............ *A61K 31/4164* (2013.01); *A61P 9/02* (2018.01)

(58) Field of Classification Search
CPC .............................. A61K 31/4164; A61P 9/02
See application file for complete search history.

(56) References Cited

U.S. PATENT DOCUMENTS

| 5,952,362 A * | 9/1999 | Cournoyer | A61P 27/16 |
|---|---|---|---|
| | | | 548/339.5 |
| 2009/0197934 A1 | 8/2009 | O'Yang et al. | |
| 2014/0121257 A1 | 5/2014 | Simpson, Jr. | |
| 2015/0374691 A1 | 12/2015 | Singer | |
| 2019/0117623 A1 | 4/2019 | Simpson, Jr. et al. | |

OTHER PUBLICATIONS

Isaacson et al., 10 Vasc. Health Risk Manag.. 169-176 (2014) (Year: 2014).*
Conlon et al., "Pharmacological Properties of 2-((R-5-Chloro-4-methoxymethylindan-1-yl)-1 H-imidazole (PF-3774076), a Novel and Selective 1A-Adrenergic Partial Agonist, in inVitro and in Vivo Models of Urethral Function", The Journal of Pharmacology and Experimental Therapeutics, Jun. 4, 2009, 330:892-901.
Isaacson et al., "Neurogenic orthostatic hypotension in Parkinson's disease: evaluation, management, and emerging role of droxidopa", Vase Health Risk Manag., Apr. 2014,10:169-176.
Drugbank, Phenylephrine. hflps://go.drugbank.com/drugs/DB00388, Apr. 27, 2018, 1 page.
PCT International Search Report and Written Opinion in International Application No. PCT/US2020/57001, dated Jan. 19, 2021, 10 pages.
Schwartz et al., "Phenylephrine Increases Cerebral Blood Flow during Low-flow Hypothermic Cardiopulmonary Bypass in Baboons", Anesthesiology, 1996, 85:380-384.
Sharma et al., "Physiology, Peripheral Vascular Resistance", Feb. 8, 2019, https://www.ncbi.nlm.nih.gov/books/NBK538308/?report=printable, 5 pages.
Vincent, "Understanding cardiac output", Critical Care, Aug. 2008, 12:174, 3 pages.

* cited by examiner

*Primary Examiner* — Timothy R Rozof
(74) *Attorney, Agent, or Firm* — DLA Piper LLP (US)

(57) ABSTRACT

In various aspects and embodiments provided are compositions and methods for a disease or disorder in a patient such as a disease or disorder that affects the brain in a patient and treating such patient.

28 Claims, No Drawings

METHODS FOR TREATING NEUROLOGICAL DISORDERS WITH $\alpha_{1A}$-AR PARTIAL AGONISTS

CROSS-REFERENCE TO RELATED APPLICATIONS

This application claims benefit of priority under 35 U.S.C. § 119(e) of U.S. Ser. No. 62/926,392, filed Oct. 25, 2019, the entire contents of which is incorporated herein by reference in its entirety.

BACKGROUND OF THE INVENTION

Field of the Invention

The present disclosure in various aspects and embodiments relates to compositions and methods for treating a brain-related disease or disorder in a patient.

Background Information

PCT Patent Application Publication No. WO2008112773 states "the application is directed to the use of droxidopa, alone or in combination with one or more additional components, for the treatment of conditions, such as neuronally mediated postural hypotension."

U.S. Pat. No. 5,952,362 discloses "various 2-imidazoline, 2-oxazoline, 2-thiazoline, and 4-imidazole derivatives of methylphenyl, methoxyphenyl, and aminophenyl alkylsulfonamides and ureas" and "includes the use of the above compounds, and compositions containing them, as alpha$_{1A/1L}$ agonists in the treatment of various disease states such as urinary incontinence, nasal congestion, priapism, depression, anxiety, dementia, senility, Alzheimer's, deficiencies in attentiveness and cognition, and eating disorders such as obesity, bulimia, and anorexia." The '362 patent discloses the compound N-[6-chloro-3-(4,5-dihydro-1H-imidazol-2-ylmethoxy)-2-methylphenyl] methanesulfonamide hydrochloride.

SUMMARY OF THE INVENTION

Current treatments for nOH (e.g., indirect sympathomimetic droxidopa/Northera or the non-selective $\alpha_1$-AR agonist midodrine) often result in a risk of supine hypertension. Accordingly, as discussed in more detail elsewhere herein it is one goal of at least some of the methods and disclosed herein to use a selective $\alpha_{1A}$-AR partial agonist to alleviate symptoms of nOH by moderately activating smooth muscles in the venous vascular branches through $\alpha_{1A}$-AR receptors, while sparing the arteriolar smooth muscles (largely $\alpha_{1B}$-AR and $\alpha_{1D}$-AR function), thus mitigating an increase peripheral vascular resistance (no 'afterload' elevation) that results in the supine hypertension caused by other nOH treatments.

As such, in a first aspect, a method is provided that includes identifying a patient diagnosed with nOH or in need of treatment for nOH and administering to said patient an $\alpha_{1A}$-AR partial agonist. In some embodiments, a patient diagnosed with nOH meet at least one or more of the following diagnostic criteria: (1) demonstrate a ≥30 mm Hg (or ≥20 mm Hg; or ≥25 mm Hg; or ≥35 mm Hg) drop in SBP within 5 minutes of standing; (2) demonstrate impaired autonomic reflexes as determined by absence of BP overshoot during phase IV of the Valsalva maneuver; (3) experience dizziness, light-headedness, or fainting when standing; and (4) have an absence of other identifiable causes of autonomic neuropathy. In some embodiments a patient diagnosed with nOH meet at least two; or at least three; or all four of the diagnostic criteria.

In another aspect, a method is provided that includes identifying a patient diagnosed with nOH or in need of treatment for nOH and administering to said patient an $\alpha_{1A}$-AR partial agonist; wherein peripheral vascular resistance in said patient is not markedly raised (no 'afterload' elevation). In a related aspect, a method is provided that includes identifying a patient diagnosed with nOH or in need of treatment for nOH and administering to said patient an $\alpha_{1A}$-AR partial agonist; wherein the supine systolic blood pressure in said patient does not rise more than 5%; or more than 10%; or more than 15%; or more than 20%; or more than 25%; or more than 30%; or more than 35%; or more than 40%; or more than 45%; or more than 50%; or more than 60%; or more than 70%; or more than 75%; or more than 80%; or more than 90%; or more than 100% as compared to the patient's blood pressure prior to administration of the $\alpha_{1A}$-AR partial agonist.

The term "partial agonist" as used herein means a ligand that acts as an agonist to a receptor but does not reach the maximal response capability of the system even at full receptor occupancy; i.e., a partial agonist produces sub-maximal activation even when occupying the total receptor population, therefore cannot produce the maximal response, irrespective of the concentration applied. In some embodiments, a partial agonist exhibits a maximum efficacy that is less than 1% or; 5%; or 10%; or 15%; or 20%; or 25%; or 30%; or 35%; or 40%; or 45%; or 50%; or 55%; or 60%; or 65%; or 70%; or 75%; or 80%; or 85% of the efficacy of a corresponding full agonist of the same receptor.

The term "$\alpha_{1A}$-AR partial agonist" as used herein means a ligand that is a partial agonist of the $\alpha_{1A}$-AR receptor. Specific examples of an $\alpha_{1A}$-AR partial agonist include R01151240 (dabuzalgron) and Compound-B. In some embodiments an $\alpha_{1A}$-AR partial agonist exhibits a maximum efficacy (or intrinsic activity, "IA") that is less than 10%; or less than 15%; or less than 20%; or less than 25%; or less than 30%; or less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 20 and 60%; or between 20 and 55%; or between 20 and 50%; or between 20 and 45%; or between 25 and 60%; or between 25 and 55%; or between 25 and 35%; or between 30 and 40%; or between 40 and 50%; or between 45 and 55%; of the intrinsic activity of a corresponding full agonist of the $\alpha_{1A}$-AR receptor (examples of a full agonist of the $\alpha_{1A}$-AR receptor include noradrenaline and amidephrine). In certain related embodiments, In some embodiments an $\alpha_{1A}$-AR partial agonist exhibits a maximum efficacy (or intrinsic activity, "IA") that is less than 30%; or less than 35%; or less than 40%; or less than 45%; or less than 50%; or less than 55%; or less than 60%; or less than 65%; or less than 70%; or less than 75%; or less than 80%; or less than 85%—but that is greater than 5%; or 10%; or 15% or 20%. Blue et al., *BJU International*, (2004) 93:162-170 (hereby incorporated by reference in its entirety) provides compositions and methods that can be used to determine partial agonism, and partial agonism of the $\alpha_{1A}$-AR receptor in particular, and demonstrates exemplary $\alpha_{1A}$-AR partial agonists. In certain embodiments, an $\alpha_{1A}$-AR partial agonist has less than 35%; or less than 40%; or less than 45%; or less than 50%; or less than 55%; or less than 60%; or less than 65%; or less than 70%; or less than 75%; or less than 80%; or less than 85%; or between 15 and 75%; or between 20 and 65%; or between 25 and 60%; or between 25 and 55%; or between 25 and 35%; or between 30 and 40%; or between 40 and 50%; or between 45 and 55% of the activity of a full agonist using the InsPs accumulation assay described in Blue et al. (see, for example, Blue et. al., Table 1 showing an intrinsic activity of 0.31 for RO 115-1240 (dabuzalgron) free base and 0.27 for RO 115-1240 (dabuzalgron) HCl salt as compared to noradrenaline in the InsPs accumulation assay). In some embodiments, an $\alpha_{1A}$-AR partial agonist has less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 25 and 60%; or between 25 and 55%; or between 25 and 35%; or between 30 and 40%; or between 40 and 50%; or between 45 and 55% of the activity of a full agonist using the FLIPR assay described in Blue et al. (see, for example, Blue et al., Table 1 showing an intrinsic activity of 0.51 for RO 115-1240 (dabuzalgron) HCl salt as compared to noradrenaline in the FLIPR assay). In many embodiments, an $\alpha_{1A}$-AR partial agonist may have a similar affinity for the $\alpha_{1A}$-AR as compared to a full agonist. The term $\alpha_{1A}$-AR partial agonist as used herein contemplates in some embodiments any pharmaceutically acceptable salt, or prodrug thereof.

In some embodiments, an $\alpha_{1A}$-AR partial agonist is a selective $\alpha_{1A}$-AR partial agonist. As used herein a "selective $\alpha_{1A}$-AR partial agonist" exhibits partial agonism for $\alpha_{1A}$-AR receptors but does not exhibit appreciable agonism for other receptors such as other $\alpha_1$-AR subtypes (e.g., $\alpha_{1B}$-AR or $\alpha_{1D}$-AR). Blue et al., *BJU International*, (2004) 93:162-170 (hereby incorporated by reference in its entirety) provides compositions and methods that can be used to determine selective agonism (and selective partial agonism), and selective agonism (and selective partial agonism) of the $\alpha_{1A}$-AR receptor in particular, and demonstrates exemplary selectivities as $\alpha_{1A}$-AR partial agonists. In some embodiments, a selective $\alpha_{1A}$-AR agonist or a selective $\alpha_{1A}$-AR partial agonist as used herein does not exhibit agonist activity for other receptors including $\alpha_{1B}$-AR or $\alpha_{1D}$-AR receptors (for example in CHO cells expressing $\alpha_{1B}$-AR or $\alpha_{1D}$-AR using the methods described in Blue et al). In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 8.0; or less than 7.5; or less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5. In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5 using the InsPs accumulation assay described in Blue et al. (see, for example, Blue et al., Table 1 showing $pEC_{50}$ of >4.0 for RO 115-1240 (dabuzalgron) free base and HCl salt for $\alpha_{1B}$-AR and $\alpha_{1D}$-AR receptors in the InsPs accumulation assay). In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 7.0; or less than 6.5; or less than 6.0; or less than 5.5; or less than 5; or less than 4.5; or less than 4; or less than 3.5; or between 2.5 and 6; or between 3 and 5.5; or between 3 and 5.0; or between 3 and 5 using the FLIPR assay described in Blue et al (see, for example, Blue et al., Table 1 showing $pEC_{50}$ of >5.0 for RO 115-1240 (dabuzalgron) free base and HCl salt for $\alpha_{1B}$-AR and $\alpha_{1D}$-AR receptors in the FLIPR accumulation assay). In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline. In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline using the InsPs accumulation assay described in Blue et al. In some embodiments a selective $\alpha_{1A}$-AR agonist or a selective $\alpha_{1A}$-AR partial agonist as used herein has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist such as noradrenaline using the FLIPR assay described in Blue et al. In some embodiments, a selective $\alpha_{1A}$-AR agonist or a selective $\alpha_{1A}$-AR partial agonist as used herein does not exhibit agonist activity for other receptors including $\alpha_{1B}$-AR or $\alpha_{1D}$-AR receptors (for example in CHO cells expressing $\alpha_{1B}$-AR or $\alpha_{1D}$-AR using the methods described in Blue et al.) at a concentration of 30 µMol/L or less; 50 µMol/L or less; 75 µMon or less; or 100 µMol/L or less. In some embodiments a selective $\alpha_{1A}$-AR agonist or a selective $\alpha_{1A}$-AR partial agonist does not bind to other receptors with a $pK_i$ higher than 5.5; or higher than 6.0; or higher than 6.5; or higher than 7.0; or higher than 7.2; or higher than 7.5; or higher than 7.8; or higher than 8.0; or higher than 9.0 (for example using methodologies described in Blue et al). In some embodiments a selective $\alpha_{1A}$-AR agonist or a selective $\alpha_{1A}$-AR partial agonist does not bind to $\alpha_{1B}$-AR or $\alpha_{1D}$-AR receptors with a $pK_i$ higher than 5.0; or higher than 5.5; or higher than 6.0; or higher than 7.0; or higher than 8.0; or higher than 9.0 (for example using methodologies described in Blue et al).

The term "dabuzalgron," or "RO1151240," or "Ro 115-1240," as used herein means the compound N-[6-chloro-3-(4,5-dihydro-1H-imidazol-2-ylmethoxy)-2-methylphenyl] methanesulfonamide, having the chemical structure as follows (see WO/2017/147532):

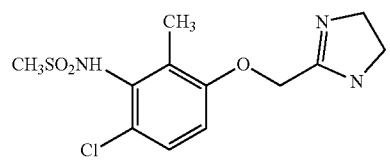

In some embodiments, term "dabuzalgron," or "RO1151240," or "Ro 115-1240," as used herein is a pharmaceutically acceptable salt (such as hydrochloride) or prodrug thereof; in other embodiments it is the free base thereof. Blue et al., *BJU International*, (2004) 93:162-170 (hereby incorporated by reference in its entirety) provides characteristics of dabuzalgron, including its partial agonistic activities on the $\alpha_{1A}$-AR and its specificity for the $\alpha_{1A}$-AR.

The term "Compound-B" as used herein means the compound N-[2-chloro-4-(4,5-dihydro-1H-imidazol-2-ylmethyl)-phenyl]-methanesulfonamide having the chemical structure as follows:

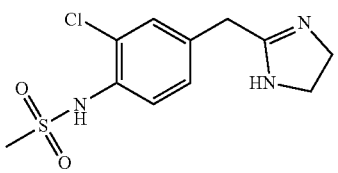 [SMILES: CS(=O)(=O)Nc1ccc(CC2=NCCN2)cc1Cl]

In some embodiments, term "Compound-B" as used herein is a pharmaceutically acceptable salt (such as hydrochloride) or prodrug thereof; in other embodiments it is the free base thereof.

The term neurogenic orthostatic hypotension (nOH) as used herein means a condition in which a subject experiences a sustained drop in blood pressure when changing positions or standing from supine or sitting postures. Symptoms of nOH can include dizziness, lightheadedness and/or a feeling that one may blackout, especially upon suddenly standing or changing position. nOH can be associated with various neurologic disorders, such as Parkinson's disease, multiple system atrophy (MSA), and pure autonomic failure (PAH). More detail on the definition, diagnosis, and characterization of nOH and its etiology is provided elsewhere herein In a further aspect, a method is provided that includes identifying a patient diagnosed with, or in need of treatment for, a disease or condition associated with low cerebral blood flow (CBF) and/or fluctuations in CBF and administering to the patient an $\alpha_{1A}$-AR partial agonist. In a further aspect, a method is provided that includes identifying a patient diagnosed with, or in need of treatment for, symptoms caused by low cerebral blood flow (CBF) and/or fluctuations in CBF and administering to the patient an $\alpha_{1A}$-AR partial agonist. In some embodiments, the disease or condition associated with low cerebral blood flow (CBF) and/or fluctuations in CBF is one or more selected from the group consisting of nOH, cognitive disorders, dementia with Lewy bodies, Parkinson's disease dementia, Alzheimer's disease, MSA, PAH. In some embodiments, the patient to be treated by the methods disclosed herein has experienced cognitive fluctuations; for example cognitive fluctuations associated with dementia with Lewy bodies (DLB) or with Parkinson's disease dementia (PDD) (see Riley and Espay, *Journal of Clinical Movement Disorders*, (2018) 5:1).

In yet another aspect, a method is provided that includes identifying a patient in need of a treatment to increase cardiac output and/or to increase venous return and administering to the patient an $\alpha_{1A}$-AR partial agonist.

In yet another aspect, a method is provided that includes (1) administering to a patient an $\alpha_{1A}$-AR partial agonist, (2) monitoring blood pressure, cardiac contractility and output, ejection fraction, and/or venous return in said patient and (3) decreasing the dose of said $\alpha_{1A}$-AR partial agonist if the supine systolic blood pressure in the patient rises above 150; or 155; or 175; or 180; or 185; or 190; or 195; or 200; or 210; or 215; or 220; or 225.

In some embodiments provided is a method of treating a patient such as contemplated herein wherein, the method includes administering to a patient an $\alpha_{1A}$-AR partial agonist at a daily dose of about 0.5 mg; or about 1 mg; or about 5 mg; or about 10 mg; or about 20 mg; or about 25 mg. In some embodiments provided is a method of treating a patient such as contemplated herein wherein, the method includes administering to a patient an $\alpha_{1A}$-AR partial agonist at a daily dose of about 0.5 mg; or about 1 mg; or about 3 mg; or about 5 mg; or about 7 mg; or about 10 mg; or about 15 mg; or about 20 mg; or about 25 mg. In some embodiments provided is a method of treating a patient such as contemplated herein wherein, the method includes administering to a patient an $\alpha_{1A}$-AR partial agonist at a dose of about 0.5 mg; or about 1 mg; or about 5 mg; or about 10 mg; or about 20 mg; or about 25 mg. In some embodiments provided is a method of treating a patient such as contemplated herein wherein, the method includes administering to a patient an $\alpha_{1A}$-AR partial agonist at a daily dose of about 0.1 µg/kg; 0.5 µg/kg; 1 µg/kg; or 5 µg/kg; or 10 µg/kg; or 15 µg/kg; or 20 µg/kg; or 25 µg/kg; or 30 µg/kg; or 35 µg/kg; or 40 µg/kg; or 45 µg/kg; or 50 µg/kg; or 60 µg/kg; or 75 µg/kg; or 100 µg/kg; or 200 µg/kg; or 250 µg/kg; or 500 µg/kg; or 750 µg/kg; or 1 mg/kg.

In some embodiments provided is a method of treating a patient such as contemplated herein wherein, the method includes administering to a patient an $\alpha_{1A}$-AR partial agonist wherein the patient takes a dose of the $\alpha_{1A}$-AR partial agonist once daily; or twice daily; or three times daily; or four times daily. In some embodiments the first dose of the $\alpha_{1A}$-AR partial agonist is taken immediately after the patient wakes in the morning. In some embodiments the first dose of the $\alpha_{1A}$-AR partial agonist is taken before noon. In some embodiments all doses of the $\alpha_{1A}$-AR partial agonist are taken before sunset. In some embodiments the last dose of the $\alpha_{1A}$-AR partial agonist for any particular day is taken at least about 1 hour; or at least about 2 hours; or at least about 3 hours; or at least about 4 hours; or at least about 5 hours; or at least about 6 hours before the patient goes to sleep at night. In some embodiments, the patient takes doses of the $\alpha_{1A}$-AR partial agonist at an interval of about 4 hours, about 5 hours; or about 6 hours. In some embodiments the patient takes a single daily dose of the $\alpha_{1A}$-AR partial agonist shortly after waking. In some embodiments the patient takes a first dose of the $\alpha_{1A}$-AR partial agonist shortly after waking and a second dose 4-6 hours later. In some embodiments the patient takes a first dose of the $\alpha_{1A}$-AR partial agonist shortly after waking and a second dose about 4 hours later and a third dose about 4 hours after the second dose. In certain embodiments, dosing earlier in the day lessens any possible negative impact of the $\alpha_{1A}$-AR partial agonist on supine systolic blood pressure.

In certain embodiments of the methods described herein, an $\alpha_{1A}$-AR partial agonist is used to treat symptomatic nOH caused by primary autonomic failure (including pure autonomic failure, multiple system atrophy and Parkinson's disease), or autonomic neuropathy (including diabetic and nondiabetic autonomic neuropathy). In another embodiment, the patient of a method as described herein has multiple system atrophy; and or the patient has Parkinson's disease.

In some embodiments of the methods as described herein, the patient has pure autonomic failure (PAF). In some embodiments of the methods as described herein the patient has multiple system atrophy (MSA). In some embodiments of the methods as described herein, the patient has symptomatic nOH caused by autonomic neuropathy.

In some embodiments of the methods as described herein, the patient exhibits one or more symptoms selected from the group consisting of slowness of movement, tremor, or rigidity (stiffness); clumsiness or incoordination; impaired speech, a croaky, quivering voice; fainting or lightheadedness due to orthostatic hypotension; bladder control problems, such as a sudden urge to urinate or difficulty emptying the bladder, stiffness, tremor, problems of balance, coordination, and autonomic nervous system dysfunction; ataxia (problems with balance and coordination), difficulty swallowing, speech abnormalities or a quavering voice, abnormal eye movements, orthostatic hypotension; dry mouth; rapid heart rate; tunnel vision; difficulty swallowing; bowel incontinence; blurry vision; urinary incontinence; constipation; anhydrosis; and sexual disfunction.

In some embodiments of the methods of the aspects and embodiments provided herein, the patient is identified as having a one or more diseases or disorders selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the of the patient is identified as having a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder).

In some embodiments the patient is a mammal. In some embodiments the patient is a human. In some embodiments the patient is a child human. In some embodiments the patient is an adult human. Child, as used herein, means a human from about 5 to 20 years of age. Adult, as used herein, means a human from about 21 years of age and older.

DETAILED DESCRIPTION OF SPECIFIC EMBODIMENTS

Some aspects and embodiments of the instant disclosure are based, at least in part, on the finding that partial agonism of an $\alpha_{1A}$-AR receptor with a relatively low dose of an $\alpha_{1A}$-AR partial agonist can increase cardiac output, resulting from improved venous return and myocardial contractility, without a concomitant substantial increase in arteriolar vascular resistance, thus resulting in an increase in blood flow to various parts of the body, including the brain. Therefore, compositions and methods are provided herein that include identifying a patient having a nOH, or a disease or disorder associated low cerebral blood flow (CBF) and/or fluctuations in CBF and administering to the patient an $\alpha_{1A}$-AR partial agonist.

In this regard, while not wishing to be bound to any one particular theory, $\alpha_{1A}$-AR receptors are preferentially found on the venous vascular branches and on the ventricular cardiomyocytes. Activation of $\alpha_{1A}$-AR receptors activates smooth muscles in the venous vascular branches, to lower venous capacitance and encourage blood return to feed the heart, and also activates the cardiomyocytes increasing pump action—a cardiotonic with a physiological inotropic effect. With increased venous return, preload is increased, thus raising the filling volume of heart; with the inotropic effect, the ejection function is enhanced, both combining to deliver more output to the arteries—and resulting in a reduction of nOH symptoms. However, unlike the indirect sympathomimetic droxidopa/Northera or the non-selective $\alpha_1$-AR agonist midodrine, an $\alpha_{1A}$-AR partial agonist, in certain embodiments will preferentially spare the arteriolar smooth muscles (largely functioning via $\alpha_{1B}$-AR and $\alpha_{1D}$-AR function), and so peripheral vascular resistance is not significantly raised (reduced 'afterload' elevation). As such, BP rise will be less strong (especially in the supine position) and the increased cardiac output will readily perfuse the organs and the brain.

Accordingly, the present disclosure includes methods and compositions for treating diseases, disorders, or conditions that are associated with, or caused by impairment (or relative decrease) in one or both of (a) cardiac output and (b) venous return.

In certain aspects and embodiments of the present disclosure compositions and methods result in an improved cognition, raised cerebral metabolic activity and/or improved inflammatory control in a patient. In some embodiments the methods described herein result in an improvement in cognition, for example as demonstrated by an improvement in a cognition test or model; a memory test; a diagnostic indicator of mental status, brain function, mental condition; a contextual learning test; or the like in the patient. Such cognitive tests, diagnostics and models are well known in the art. In various aspects and embodiments, any of many accepted contextual learning tests for animals or humans can be used to assess baseline cognitive function and/or to measure or quantify improved cognitive function. In some embodiments, the compositions and methods described herein may result in an improvement one or more tests, diagnostics and models as follows. Likewise, for the raised cerebral metabolic activity and improved inflammatory control these in certain embodiments may be imaged via special methodologies including MRI (using arterial spin labelling [ASL] and blood oxygenation level dependent [BOLD], as well as positron emission tomography approaches such as FDG-PET, and via sampling of cerebrospinal fluid (CSF) allowing measures of inflammatory cytokines and markers of glial cell activation.

Orthostatic hypotension (OH), also known as postural hypotension, is a form of low blood pressure which occurs when a person stands up. In medical terms, OH is defined as a fall in systolic blood pressure of at least 20 or 30 mm Hg, or diastolic blood pressure of at least 10 mm Hg within three minutes of a postural change from supine to upright position (*Neurology* 1996; 46:1470). OH can produce a wide variety of symptoms including dizziness, lightheadedness and syncope (fainting), as well as discomfort in the upper chest and shoulder region ('coat-hanger' pain). Due to these symptoms, OH often curtails or even prevents daily activities that require standing or walking. Additionally, OH is associated with increased morbidity and mortality. See, for example, Jones et al, *Expert Review of Cardiovascular Therapy*, 2015;

13:11, 1263-1276; Kuritzky et al., *Postgrad. Med.* 2015; 127(7):702-715; and Low et al, *J. Clin. Neurol.,* 2015; 11(3):220-226.

The underlying causes of OH can be broadly divided into neurogenic and non-neurogenic categories. Neurogenic orthostatic hypotension (nOH) is a form of OH involving the nervous system, e.g., OH caused by a peripheral or central neurologic disorder, such as primary autonomic failure (including pure autonomic failure, multiple system atrophy, and Parkinson's disease), and autonomic neuropathy (dysautonomia) (including diabetic and nondiabetic autonomic neuropathy) (Arbique et al., *JAMDA* 15 (2014) 234-239). Such disorders can cause a deficiency or dysregulation of norepinephrine which is the primary neurotransmitter that regulates blood pressure in response to postural changes (Loavenbruck et al, *Curr. Med. Res. Opin.,* 2015; 31:2095-2104). As a result, the autonomic nervous system fails to properly regulate blood pressure during a postural change and the patient experiences a significant fall in blood pressure resulting in, e.g., dizziness, lightheadedness, or syncope.

Accordingly, the management of the nOH condition requires, most fundamentally, increasing cerebral blood flow (CBF) in the context of an otherwise pathological fall in blood pressure, on supine to standing posture changes in patients. In various aspects and embodiments of the compositions and methods provided herein, an $\alpha_{1A}$-AR partial agonist is administered to a patient having nOH, and the actions of the partial agonist make less frequent and less severe associated signs and symptoms of nOH, including light-headedness/dizziness, pre-syncopal symptoms, syncope/blackout, and 'coat-hanger pain'. By maintaining better CBF, patients in some embodiments will also maintain improved cognitive function, especially those prone to 'fluctuations' which are commonly seen in the parkinsonism (or 'synucleinopathy') family of conditions often typically associated with nOH. Symptoms/tests/screening for nOH and descriptions of some treatments can be found in Eschlbock et al, *J Neural Tansm,* (2017) 124:1567-1605 and Gibbons et al, *J Neurol,* (2017) 264:1567-1582.

One objective of certain more traditional nOH treatments is to increase levels of norepinephrine in patients. One way to increase norepinephrine levels is to administer an agent that generates norepinephrine. For example, droxidopa (L-threo-3-4-dihydroxyphenylserine) is an amino acid that is converted by decarboxylation into norepinephrine in both the central and the peripheral nervous systems thereby increasing levels of norepinephrine (Kaufmann et al., *Circulation,* 2003; 108:724-728; Kaufmann, *Clin. Auton. Res.* (2008) 18[Suppl 1]:19-24); and Isaacson et al., *Vascular Health and Risk Management,* 2014, 10:169-176). Droxidopa is approved in the U.S. for the treatment of orthostatic dizziness, light-headedness, or the "feeling that you are about to black out" in adult patients with symptomatic nOH caused by primary autonomic failure (Parkinson's disease, multiple system atrophy, and pure autonomic failure), dopamine beta-hydroxylase deficiency, and nondiabetic autonomic neuropathy. The main side effect of droxidopa is supine hypertension and there is a black box warning in the prescribing information for this medication due to this serious side effect.

Alternatively, norepinephrine levels can be increased in patients by inhibiting the norepinephrine transporter which is responsible for norepinephrine reuptake. For example, atomoxetine is a selective norepinephrine reuptake inhibitor approved in the U.S. for treatment of attention-deficit hyperactivity disorder (ADHD). Atomoxetine has been shown to increase blood pressure in patients with central autonomic failure (Ramirez et al., *Hypertension,* 2014; 64:1235-40; and Shibao et al., *Hypertension,* 2007; 50:47-53). Atomoxetine, however, is metabolized primarily through the CYP2D6 enzymatic pathway and therefore, its pharmacokinetic properties are variable depending on whether the patient has reduced CYP2D6 activity (poor metabolizer) or normal CYP2D6 activity (extensive metabolizer) (Ring et al., *Drug Metabolism and Distribution,* 2002, 30:319-323). The prescribing information for atomoxetine also includes a number of warnings about possible drug-drug interactions. Additionally, when used to treat ADHD, atomoxetine is associated with a number of gastrointestinal adverse effects including dry mouth and nausea. Atomoxetine has not been approved for the treatment of nOH.

Other agents that historically have been used to treat nOH include the $\alpha_1$-adrenoceptor full agonist, midodrine (and its active non-selective agonist metabolite, desglymidodrine); the synthetic mineralocorticoid, fludrocortisone; and the cholinesterase inhibitor, pyridostigmine. The side effects of these agents can include, for midodrine, supine hypertension, paraesthesias (including scalp-tingling), piloerection (goose bumps), and urinary urgency or retention; for fludrocortisone, hypokalemia, headaches, peripheral edema, heart failure and supine hypertension; and for pyridostigmine, abdominal discomfort and urinary urgency.

In some embodiments, nOH can be diagnosed, for example, by the patient reporting signs and symptoms of nOH, including sway, light-headedness/dizziness, pre-syncopal symptoms, syncope/blackout, and 'coat-hanger pain'. Neurally-mediated hypotension in some embodiments can be diagnosed by using the so-called "tilt table test", which reveals a drop in blood pressure on moving a subject to near-upright position, and may reveal a drop in heart rate. In some cases, neurally-mediated hypotension (NMH) is diagnosed by a drop in blood pressure alone. In other cases, such diagnosis is only made when a drop in blood pressure also accompanies a drop in heart rate. The tilt table test measures heart rate and blood pressure while lying down (during resting state), then standing at a 70 degree angle for 45 minutes. The patient is lowered while medication, such as isoproterenol, is administered through an IV to increase the heart rate to about 10% above the resting heart rate and then the patient is returned to the 70 degree angle for 15 minutes. The medication is increased to further increase the heart rate, and the patient is returned to the upright position for 10 minutes. Preferably, the test environment is quiet and non-stimulating to eliminate distractions. The patient may be required to fast after midnight prior to the test (to reduce incidence of nausea and vomiting). The patient is strapped on the table to avoid injury in case of fainting and also to decrease the human nature of compensating for the blood pooling in the legs by "fidgeting". Patient vital signs are monitored throughout the tilt table test, and the test is determined to have a positive result for NMH if there is a "significant" drop in blood pressure and a drop in heart rate. As noted above, some physicians consider a positive diagnosis with a drop in blood pressure alone.

In one embodiment, an $\alpha_{1A}$-AR partial agonist is used to treat symptomatic nOH caused by primary autonomic failure (including pure autonomic failure, multiple system atrophy and Parkinson's disease), or autonomic neuropathy (including diabetic and nondiabetic autonomic neuropathy). In one embodiment, an $\alpha_{1A}$-AR partial agonist is used to treat symptomatic nOH caused by primary autonomic failure. In this embodiment, the patient may be diagnosed with pure autonomic failure, multiple system atrophy and/or Parkinson's disease. In one embodiment, the patient has pure autonomic failure. In another embodiment, the patient has multiple system atrophy. And in another embodiment, the patient has Parkinson's disease. Primary autonomic failure (also called primary dysautonomia) is a category of dysautonomia, i.e., a condition in which the autonomic nervous system does not function properly. In primary autonomic failure, the autonomic dysfunction occurs as a primary condition as opposed to a secondary condition resulting from another disease, such as diabetes. For example, autonomic failure is typically categorized as "primary" when it results from a chronic condition characterized by degeneration of the autonomic nervous system or where autonomic failure is the predominant symptom and its cause is unknown. Conditions categorized as primary autonomic failure include pure autonomic failure, multiple system atrophy, and Parkinson's disease.

Pure autonomic failure (PAF), also known as Bradbury-Eggleston syndrome or idiopathic orthostatic hypotension, is a degenerative disease of the autonomic nervous system. A primary symptom of PAF is orthostatic hypotension. Other symptoms may include decreased sweating, heat intolerance, urinary retention, bladder spasms (possibly causing incontinence), erectile dysfunction, fecal incontinence or constipation, and pupillary abnormalities. The cause of PAF is not completely understood, but the loss of cells in the intermediolateral column of the spinal cord has been documented in patients with PAF. Additionally, PAF may be related to abnormal accumulation of alpha-synuclein.

Parkinson's disease (PD) is a chronic and progressive movement disorder. The cause is unknown, but PD involves the malfunction and death of neurons in an area of the midbrain called the substantia nigra. These neurons produce dopamine which plays a key role in movement and coordination. As PD progresses, the amount of dopamine produced in the brain decreases resulting in motor control and coordination problems. Symptoms include tremor, rigidity, slowness of movement, and postural instability. However, some PD patients also experience non-motor symptoms including orthostatic hypotension due to alterations in the autonomic nervous system, i.e., PD plus symptoms of nOH. Additionally, some patients with PD symptoms have a condition known as Parkinson-plus syndromes (or disorders of multiple system degeneration). Parkinson-plus syndromes is a group of neurodegenerative diseases that produce the classical symptoms of PD (tremor, rigidity, akinesia/bradykinesia, and postural instability) with additional features that distinguish them from simple idiopathic PD. Clinical features distinguishing Parkinson-plus syndromes from idiopathic PD include symmetrical onset, a lack of or irregular resting tremor, and a reduced response to dopaminergic drugs (including levodopa). Additional features include bradykinesia, early-onset postural instability, increased rigidity in axial muscles, dysautonomia, alien limb syndrome, supranuclear gaze palsy, apraxia, involvement of the cerebellum including the pyramidal cells, and in some instances significant cognitive impairment.

Multiple system atrophy (MSA), also known as Shy-Drager syndrome, is a progressive neurodegenerative disorder characterized by a combination of symptoms that affect both the autonomic nervous system and movement. The initial symptoms of MSA are often difficult to distinguish from the initial symptoms of Parkinson's disease and include slowness of movement, tremor, or rigidity (stiffness); clumsiness or incoordination; impaired speech, a croaky, quivering voice; fainting or lightheadedness due to orthostatic hypotension; bladder control problems, such as a sudden urge to urinate or difficulty emptying the bladder. MSA is divided into two different types depending on the most prominent symptoms at the time an individual is evaluated: the parkinsonian type (MSA-P), with primary characteristics similar to Parkinson's disease (such as moving slowly, stiffness, and tremor) along with problems of balance, coordination, and autonomic nervous system dysfunction; and the cerebellar type (MSA-C), with primary symptoms featuring ataxia (problems with balance and coordination), difficulty swallowing, speech abnormalities or a quavering voice, and abnormal eye movements. The cause of MSA is unknown. A distinguishing feature of MSA is the accumulation of the protein alpha-synuclein in glia, the cells that support nerve cells in the brain. These deposits of alpha-synuclein particularly occur in oligodendroglia, a type of cell that makes myelin (a coating on nerve cells that lets them conduct electrical signals rapidly). A recent study indicates that a prion form of the alpha-synuclein protein may be the cause of the disease (Prusiner et al, *PNAS*, (2015) 112: E5308-17).

In one embodiment, an $\alpha_{1A}$-AR partial agonist is used is used to treat symptomatic nOH caused by autonomic neuropathy. Autonomic neuropathy, or dysautonomia, refers to various conditions in which the autonomic nervous system (ANS) does not work properly. Autonomic neuropathy is a type of neuropathy affecting the nerves that carry information from the brain and spinal cord to the heart, bladder, intestines, sweat glands, pupils, and blood vessels. The primary symptoms of autonomic neuropathy, which can vary between individuals, include: orthostatic hypotension; dry mouth; rapid heart rate; tunnel vision; difficulty swallowing; bowel incontinence; blurry vision; urinary incontinence; constipation; anhydrosis; and sexual dysfunction. Autonomic neuropathy may be due to inherited or degenerative neurologic diseases (primary dysautonomia) or it may occur due to injury of the autonomic nervous system from an acquired disorder (secondary dysautonomia).

Riley and Espay, *Journal of Clinical Movement Disorders*, (2018) 5:1 described a patient having Parkinson's disease dementia (PDD) that experienced cognitive fluctuations that correlated with the patient's blood pressure. Accordingly, in some aspects and embodiments, a method is provided that includes identifying a patient diagnosed with, or in need of treatment for, a disease or condition associated with low cerebral blood flow (CBF) and/or fluctuations in CBF and administering to the patient an $\alpha_{1A}$-AR partial agonist; wherein the patient treated by the methods disclosed herein has experienced cognitive fluctuations; for example cognitive fluctuations associated with dementia with Lewy bodies (DLB) or with Parkinson's disease dementia (PDD).

There are many contextual learning tests used that are acknowledged and/or accepted in the art that in various embodiments may be used in conjunction with the compositions and methods disclosed herein to assess baseline cognitive function and/or to measure or quantify improved cognitive function in human subjects. For example, the contextual learning test used may be based upon single task learning, multiple task learning or spatial contextual memory. Contextual learning test evaluations based upon spatial contextual memory may be advantageous in assessing, for example, how well an individual is able to navigate a shopping mall, his or her neighborhood or a city transit or subway system as well as assessing any improvements in the ability to execute these tasks resulting from the treatment methods described herein.

An example of a simple spatial contextual learning test is contextual cuing, where humans learn to use repeated spatial configurations to facilitate a target search. A higher order spatial contextual learning test is serial learning, where humans learn to use subtle sequence regularities to respond more quickly and accurately to a series of events. See, for example, J. H. Howard Jr., et al., Neuropsychology, Vol. 18(1), January 2004, 124-134.

In some embodiments, cognition may be evaluated using the Mini-Mental State Examination (MMSE) and/or the Montreal Cognitive Assessment (MOCA).

Arizona Cognitive Test Battery (ACTB). A testing protocol that may be used in various embodiments is the Arizona Cognitive Test Battery (ACTB). See Edgin, J., et al. J. Neurodevelop. Disord. (2010) 2: 149-164. The ACTB has been developed specifically to assess the cognitive phenotype in DS, and includes various tests with various task demands and links with brain function. In more detail, tests are included for: 1) benchmarks, such as KBIT II verbal subscale and KBIT II non-verbal subscale IQ tests, 2) hippocampal function, 3) prefrontal function, 4) cerebellar function, 5) Finger sequencing tasks, 6) NEPSY visuomotor precision and 7) simple reaction time.

A correlation of domain/test, test description and primary ability assessed in accordance with the ACTB is provided below:

| Domain/Test | Description | Primary Ability Assessed |
| --- | --- | --- |
| 1) Benchmark KBIT-II verbal subscale | Points to pictures based on word or phrase | Verbal comprehension |
| KBIT-II nonverbal subscale | Semantic or visuo-spatial pattern completion | Problem solving |
| 2) CANTAB spatial span | Touching boxes in order of changing color on screen | Immediate memory for spatial-temporal sequence |
| 3) Prefrontal Modified dots task | Press button below a cat, shifts to new rule, press across screen for a frog, etc. | Inhibitory control working memory |
| 4) CANTAB IED | Forced-choice discrimination task with change in relevant dimension | Set-shifting |
| 5) Hippocampal CANTAB paired associates | Recall for hidden abstract patterns | Spatial associative memory |
| 6) Virtual computer-generated arena | Navigation of a virtual arena (via joystick) to find a hidden target | Spatial memory |
| 7) Cerebellar Finger-sequencing task | Sequences generated by tapping a number of fingers (1, 2, 3, 4) to a lever in succession | Motor sequencing |
| 8) NEPSY visuo-motor precision | Follows two tracks with a pen | Visuo-motor tracking, hand-eye coord. |
| 9) CANTAB simple reaction time | Participants press button in response to a box presented on a screen | Motor response time and attention |

With respect to the agents described herein, the terms "modulate" and "modulation" refers to the upregulation (i.e., activation or stimulation) or downregulation (i.e., inhibition or suppression) of a response. A "modulator" is an agent, compound, or molecule that modulates, and may be, for example, an agonist, antagonist, activator, stimulator, suppressor, or inhibitor. The terms "inhibit", "reduce", remove as used herein refer to any inhibition, reduction, decrease, suppression, downregulation, or prevention in expression, activity or symptom and include partial or complete inhibition of activity or symptom. Partial inhibition can imply a level of expression, activity or symptom that is, for example, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the uninhibited expression, activity or symptom. The terms "eliminate" or "eradicate" indicate a complete reduction of activity or symptom.

As used herein, the term "a disorder" or "a disease" refers to any derangement or abnormality of function; a morbid physical or mental state. See Dorland's Illustrated Medical Dictionary, (W.B. Saunders Co. 27th ed. 1988).

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

In some embodiments, contemplated methods may include for example, administering prodrugs of the compounds described herein, or a pharmaceutical composition thereof. The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). In some embodiments, the prodrug structures are constructed according to the disclosure in U.S. Pat. No. 9,849,134, which is incorporated by reference herein in the entirety.

For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N, N—$(C_{1-2})$alkylamino-$(C_{2-3})$alkyl (such as (3-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino $(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-(($C_{1-6}$)

alkylcarbonyloxy)ethyl, 1-methyl-1-(($C_{1-6}$)alkylcarbonyloxy)ethyl ($C_{1-6}$)alkoxycarbonyloxy)methyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-amino-alkylcarbonyl α-aminoalkylcarbonyl, where each α-aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., Molecules 2008, 13, 519 and references therein.

"Therapeutically effective amount" as used herein means the amount of a compound or composition (such as described herein) that causes at least one desirable change in a cell, population of cells, tissue, individual, patient or the like. In some embodiments a therapeutically effective amount as used herein means the amount of a compound or composition (such as described herein) that prevents or provides a clinically significant change in a disease or condition (e.g., reduce by at least about 30 percent, at least about 50 percent, or at least about 90 percent) or in one or more features of a disease or condition described herein.

Dosage, Administration and Pharmaceutical Formulation

The term "pharmaceutically-accepted salts" means acid addition salts that are commonly used in human or veterinary medicine and are deemed safe for use. Examples for the present disclosure include, but are not limited to, salts obtained from the following acids: acetic, ascorbic, benzenesulfonic, benzoic, camphosulfonic, citric, ethanesulfonic, edisylic, fumaric, gentisic, gluconic, glucoronic, glutamic, hippuric, hydrobromic, isethionic, lactic, nitric, phosphoric, succinic, sulfuric and tartaric, for example. Any hydrated forms of such salts are also included in this definition. Thus, for example, both fumarate and hemifumarate salts are specifically contemplated as well as any hydrates thereof. For example, fumarate dihydrate may be specifically mentioned.

The pharmaceutical preparation in some embodiments may be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

For a binding agent, composition, or compound according to the present disclosure, the dosage form may optionally be a liquid dosage form. Solutions can be prepared in water suitably mixed with a surfactant such as hydroxypropylcellulose or an emulsifier such as polysorbate. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. Formulations optionally contain excipients including, but not limited to, a buffering agents, an anti-oxidant, a stabilizer, a carrier, a diluent, and an agent for pH adjustment. The pharmaceutical forms suitable for injectable use include sterile aqueous solutions or dispersion and sterile powders for the extemporaneous preparation of sterile injectable solutions or dispersions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

In certain embodiments, an agent in accordance with the methods provided herein is administered subcutaneously (s.c.), intravenously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g. 1, or 2 or 3 times).

EXAMPLES

The present disclosure will be further described in the following examples, which do not limit the scope of the present disclosure.

Example 1: Treatment of a Patient Having NOH

Patients between the age of 40 and 80 years old that have been diagnosed with symptomatic orthostatic hypotension due to pure autonomic failure, multiple system atrophy or Parkinson's disease (i.e., PD plus symptoms) present for treatment. At the time of presentation, autonomic function testing is conducted to confirm the diagnosis of autonomic dysfunction including sinus arrhythmia and the Valsalva maneuver. The patients: (1) demonstrate a ≥30 mm Hg drop in SBP within 5 minutes of standing; (2) demonstrate impaired autonomic reflexes as determined by absence of BP overshoot during phase IV of the Valsalva maneuver; (3)

experience dizziness, light-headedness, or fainting when standing; and (4) have an absence of other identifiable causes of autonomic neuropathy.

The patients are given 5 mg dabuzalgron oral tablets and are instructed to take one tablet shortly after waking up in the morning and a second tablet 4-6 hours later each day.

Some patients return for a follow-up visit after one week of treatment. It is expected that the symptoms of nOH improve as compared to the first visit before dabulzagron treatment. In the follow-up visit supine systolic blood pressure (SSBP) may be determined. It is expected that patients taking dabulzagron will not experience a substantial rise in SSBP; and/or the rise in SSBP is less that that observed in patients taking midodrine or droxidopa for nOH.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

Various embodiments of the present disclosure may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the disclosure described above are intended to be merely exemplary; numerous variations and modifications will be apparent to those skilled in the art. All such variations and modifications are intended to be within the scope of the present disclosure as defined in any appended claims.

All publications, patent applications, patents, and other references mentioned herein are expressly incorporated by reference in their entirety, to the same extent as if each were incorporated by reference individually. In case of conflict, the present specification, including definitions, will control.

Although the invention has been described with reference to the above examples, it will be understood that modifications and variations are encompassed within the spirit and scope of the invention. Accordingly, the invention is limited only by the following claims.

What is claimed is:

1. A method comprising administering to a patient diagnosed with nOH or in need of treatment for nOH, an α1A-AR partial agonist, wherein the agonist is RO1151240 (dabuzalgron) or Compound B.

2. The method of claim 1, wherein said patient meets at least one or more of the following diagnostic criteria: (1) demonstrate a >20-30 mm Hg drop in SBP within 5 minutes of standing; (2) demonstrate impaired autonomic reflexes as determined by absence of BP overshoot during phase IV of the Valsalva maneuver; (3) experience dizziness, light-headedness, or fainting when standing; and (4) have an absence of other identifiable causes of autonomic neuropathy.

3. The method of claim 1, wherein peripheral vascular resistance in said patient is not significantly raised following administration of said $\alpha_{1A}$-AR partial agonist.

4. The method of claim 1, wherein the supine systolic blood pressure in said patient does not rise more than 5%; or more than 10%; or more than 15%; or more than 20%; or more than 25%; or more than 30%; or more than 35%; or more than 40%; or more than 45%; or more than 50%; or more than 60%; or more than 70%; or more than 75%; or more than 80%; or more than 90%; or more than 100% as compared to the patient's blood pressure prior to administration of the $\alpha_{1A}$-AR partial agonist.

5. The method of claim 1, wherein said nOH in said patient is associated with one or more of Parkinson's disease, multiple system atrophy, and pure autonomic failure.

6. A method for treating a disease or condition associated with low cerebral blood flow (CBF) and/or fluctuations in CBF, said method comprising identifying a patient diagnosed with, or in need of treatment for, a disease or condition associated with low cerebral blood flow (CBF) and/or fluctuations in CBF; and administering to said patient an α1-AR partial agonist, wherein the agonist is RO1151240 (dabuzalgron) or Compound B.

7. The method of claim 6, wherein said patient has been diagnosed with dementia with Lewy bodies (DLB) or with Parkinson's disease dementia (PDD).

8. A method of treating a patient, said method comprising identifying a patient in need of a treatment to increase cardiac output and/or to increase venous return and administering to said patient an α1A-AR partial agonist, wherein the agonist is RO1151240 (dabuzalgron) or Compound B.

9. The method of claim 1, wherein said $\alpha_{1A}$-AR partial agonist is a selective $\alpha_{1A}$-AR partial agonist.

10. The method of claim 1, wherein said $\alpha_{1A}$-AR partial agonist exhibits a maximum efficacy that is less than 10%; or less than 15%; or less than 20%; or less than 25%; or less than 30%; or less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 25 and 60%; or between 25 and 55%; or between 25 and 35%; or between 30 and 40%; or between 40 and 50%; or between 45 and 55% of the intrinsic activity of a corresponding full agonist of the $\alpha_{1A}$-AR receptor.

11. The method of claim 1, wherein said $\alpha_{1A}$-AR partial agonist exhibits a maximum efficacy that is less than 10%; or less than 15%; or less than 20%; or less than 25%; or less than 30%; or less than 35%; or less than 40%; or less than 45%; or less than 50%; or less than 55%; or less than 60%; or less than 65%; or less than 70%; or less than 75%; or less than 80%; or less than 85% or between 15 and 75%; or between 20 and 65%; or between 25 and 60%; or between 25 and 55%; or between 25 and 35%; or between 30 and 40%; or between 40 and 50%; or between 45 and 55% of the intrinsic activity of noradrenaline.

12. The method of claim 1, wherein said $\alpha_{1A}$-AR partial agonist has a $pEC_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of a non-selective agonist.

13. The method of claim 1, wherein said $\alpha_{1A}$-AR partial agonist has a pEC$_{50}$ for $\alpha_{1B}$-AR and $\alpha_{1D}$-AR receptors that is less than 85%; or less than 80%; or less than 75%; or less than 65%; or less than 60%; or less than 55%; or less than 50% of that of noradrenaline.

14. The method of claim 6, wherein the supine systolic blood pressure in said patient does not rise more than 5%; or more than 10%; or more than 15%; or more than 20%; or more than 25%; or more than 30%; or more than 35%; or more than 40%; or more than 45%; or more than 50%; or more than 60%; or more than 70%; or more than 75%; or more than 80%; or more than 90%; or more than 100% as compared to the patient's blood pressure prior to administration of the $\alpha_{1A}$-AR partial agonist.

15. The method of claim 1, further comprising monitoring blood pressure and/or venous return in said patient and decreasing the dose of said $\alpha_{1A}$-AR partial agonist if the supine systolic blood pressure in the patient rises above 150; or 155; or 175; or 180; or 185; or 190; or 195; or 200; or 210; or 215; or 220; or 225.

16. The method of claim 1, wherein said patient takes a dose of the $\alpha_{1A}$-AR partial agonist once daily; or twice daily; or three times daily; or four times daily.

17. The method of claim 1, wherein said patient takes a first daily dose of said $\alpha_{1A}$-AR partial agonist immediately after the patient wakes in the morning.

18. The method of claim 1, wherein the dabuzalgron is administered at a dose selected from the group consisting of about 0.5 mg, about 1 mg, about 3 mg, about 5 mg, about 7 mg, about 10 mg, about 15 mg, about 20 mg and about 25 mg.

19. The method of claim 1, wherein dabuzalgron maintains blood flow to the brain.

20. The method of claim 1, wherein dabuzalgron increases preload and/or increases ventricular contractility.

21. The method of claim 1, wherein administration increases cardiac output, without a concomitant substantial increase in arteriolar vascular resistance.

22. The method of claim 18, wherein the dose is 0.5 mg.
23. The method of claim 18, wherein the dose is 1 mg.
24. The method of claim 18, wherein the dose is 3 mg.
25. The method of claim 18, wherein the dose is 5 mg.
26. The method of claim 18, wherein the dose is 7 mg.
27. The method of claim 18, wherein the dose is 10 mg.
28. The method of claim 18, wherein the dose is 15 mg.

* * * * *